(12) United States Patent
Tchakalova et al.

(10) Patent No.: US 10,894,934 B2
(45) Date of Patent: Jan. 19, 2021

(54) RINGING GEL COMPOSITION

(71) Applicant: FIRMENICH SA, Geneva (CH)

(72) Inventors: Vera Tchakalova, Geneva (CH); Claudie Bellouard, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/342,520

(22) PCT Filed: Oct. 17, 2017

(86) PCT No.: PCT/EP2017/076462
§ 371 (c)(1),
(2) Date: Apr. 16, 2019

(87) PCT Pub. No.: WO2018/073238
PCT Pub. Date: Apr. 26, 2018

(65) Prior Publication Data
US 2019/0241841 A1 Aug. 8, 2019

(30) Foreign Application Priority Data
Oct. 18, 2016 (EP) .................................. 16194399

(51) Int. Cl.
C11D 17/00 (2006.01)
C11D 3/50 (2006.01)
(Continued)

(52) U.S. Cl.
CPC ............ C11D 3/505 (2013.01); A61Q 13/00 (2013.01); C11D 1/72 (2013.01); C11D 3/2079 (2013.01);
(Continued)

(58) Field of Classification Search
CPC ............................... C09K 8/584; C09K 8/602
See application file for complete search history.

(56) References Cited

U.S. PATENT DOCUMENTS 9,328,319 B2   5/2016 Ravidat et al.
2002/0034489 A1   3/2002 Wiegland et al.
(Continued)

FOREIGN PATENT DOCUMENTS

EP   0 682 104 A2   11/1995
EP   1 213 007 A2   6/2002
(Continued)

OTHER PUBLICATIONS

International Search Report and Written Opinion, Appl. No. PCT/EP2017/076462, dated Jan. 22, 2018.

Primary Examiner — John R Hardee
(74) Attorney, Agent, or Firm — Armstrong Teasdale LLP

(57) ABSTRACT

The present invention relates to the field of liquid solubilizing systems. More specifically, the present invention relates to a ringing gel composition, one that is a self-thickened composition having a viscoelastic behavior and a viscosity comprised between 0.1 and 1000 Pa·s at 20° C. at 0.01 $s^{-1}$ shear rate. The ringing gel has an aqueous phase, a surfactant system of one or more non-ionic surfactant(s), a linker and an oil phase that includes a hydrophobic active ingredient such as a perfume. Consumer products that contain the ringing gel composition, such as a self-thickened liquid laundry scent booster are also part of the present invention.

20 Claims, 4 Drawing Sheets

(51) Int. Cl.
*A61Q 13/00* (2006.01)
*C11D 1/72* (2006.01)
*C11D 3/20* (2006.01)

(52) U.S. Cl.
CPC .......... *C11D 3/2093* (2013.01); *C11D 17/003* (2013.01); *C11D 17/0039* (2013.01)

(56) References Cited

U.S. PATENT DOCUMENTS

| | | |
|---|---|---|
| 2003/0012759 A1 | 1/2003 | Bowen-Leaver et al. |
| 2007/0071780 A1 | 3/2007 | Dubois et al. |
| 2009/0107681 A1* | 4/2009 | Hough ............... C09K 8/44 166/308.3 |
| 2009/0111716 A1* | 4/2009 | Hough ............... C09K 8/584 507/214 |
| 2011/0268683 A1 | 11/2011 | Hawkins et al. |
| 2014/0017307 A1 | 1/2014 | Marzouk et al. |

FOREIGN PATENT DOCUMENTS

| | | |
|---|---|---|
| EP | 0 813 862 B1 | 12/2002 |
| EP | 2 300 146 B1 | 3/2017 |
| EP | 2 579 976 B1 | 8/2017 |
| WO | 00/076460 A2 | 12/2000 |
| WO | 2005/017080 A2 | 2/2005 |
| WO | 2007/004166 A1 | 1/2007 |
| WO | 2010/048154 A2 | 4/2010 |
| WO | 2011094714 A1 | 8/2011 |
| WO | 2013068255 A1 | 5/2013 |
| WO | 2014085286 A1 | 6/2014 |

\* cited by examiner (a) (b)

RINGING GEL COMPOSITION

This application is a 371 filing of International Patent Application PCT/EP2017/076462 filed Oct. 17, 2017, which claims the benefit of European patent application no. 16194399.8 filed Oct. 18, 2017.

TECHNICAL FIELD

The present invention relates to the field of liquid solubilizing systems. More specifically, the present invention relates to a ringing gel composition i.e. a self-thickened composition having a viscoelastic behavior and a viscosity comprised between 0.1 and 1000 Pa·s at 20° C. at 0.01 s$^{-1}$ shear rate, said ringing gel comprising an aqueous phase, a surfactant system essentially consisting of non-ionic surfactant(s), a linker and an oil phase comprising an hydrophobic active ingredient, preferably a perfume.

Consumer products comprising or consisting of said ringing gel composition, such as a self-thickened liquid laundry scent booster are also part of the present invention.

BACKGROUND OF THE INVENTION

Fragrances play an important role in the perception of products performance and thus they often determine the consumer's choice for a given product. In detergents, hard surface cleaners or personal- or body-care products, the fragrances are incorporated as a free oil and/or encapsulated in microcapsules in order to deliver a pleasant odor to the skin or to the fabrics.

When the fragrances are present as a free oil, the main challenges are the enhanced fragrance performance and the long-lasting of the olfactive perception during and after use, e.g. after rinsing and drying of the skin or the fabrics.

When microcapsules are used, providing a stable dispersion of those microcapsules in the consumer product is one of the key parameters for the product quality.

Combinations of a free fragranced oil and fragrance-containing microcapsules into a given consumer product can deliver benefits such as solubilisation of higher fragrance quantity, highly enhanced fragrance performance or controlled release of the fragrance under stimuli such as temperature, friction, oxidation and others. On the other hand, difficulties related to successful homogenous solubilisation of the free oil and stable dispersion of the microcapsules are cumulated.

In the patent publication US2007071780, the fragrance performance is enhanced by an appropriate combination of perfumery ingredients composing the final fragrance.

In the publication WO2005/017080, a microemulsion containing non-ionic surfactants, alkyl pyrrolidone and block copolymer is used for enhancing deposition of fragrance on fabric from laundry or fabric softener consumer product. The increased contact surface of the fragranced droplets in the microemulsion as well as the good wetting assured by the wetting agent alkyl pyrrolidone are claimed to be the reason for the enhanced fragranced deposition and thus performance.

EP0813862 discloses a microemulsion formulation containing high quantity of non-encapsulated fragrance for fabric softener application.

However, the microemulsion approach does not allow the successful stable suspension of microcapsules due to the low Newtonian viscosity of the formulation.

Usually, the appropriate viscosity necessary for a stable suspension of microcapsules is achieved by using external structuring systems such as acrylate polymer, structuring gums (xanthan gum), starch, agar, hydroxyl allyl cellulose. Examples of such approaches are disclosed respectively in US2014/0017307 and WO2010/048154.

Self-thickening formulations composed mainly of lyotropic liquid-crystalline phases are also disclosed in the literature.

For example, WO 2014/085286 discloses enhanced fragrance performance of fragrance containing capsules dispersed into lyotropic liquid crystalline surfactant phases before being dispersed into a consumer product. In this document, the surfactant lyotropic liquid crystalline phases are oil-continuous liquid crystalline phase comprising both anionic and cationic surfactants, which is a limiting factor for the compatibility of the composition in a consumer product. Furthermore, another disadvantage of the lyotropic liquid-crystalline phases is that they exhibit a high viscosity, requiring relatively high cost shearing.

U.S. Pat. No. 9,328,319 relates to a fabric care microemulsion having perfume microcapsules. However, said composition requires the use of a thickener to suspend microcapsules within the composition.

Attractive alternative solubilizing systems are the so-called "ringing gels", which are self-thickened formulations with viscosity lower than that of liquid crystalline phases.

US2011/0268683 discloses a pourable ringing gel surfactant composition comprising a mixture of at least one anionic surfactant having a $C_8$-$C_{18}$ carbon chain and at least one zwitterionic or amphoteric surfactant having a $C_8$-$C_{18}$ carbon chain.

Another example of ringing gel is disclosed in US2002/034489 which describes a ringing gel composition comprising (a) a surfactant phase; (b) an oil phase; and (c) a benefit agent.

The surfactant phase in this document contains at least one anionic surfactant, at least one amphoteric, at least one non-ionic surfactant.

The publication US 2003/0012759 discloses a method of making a ringing nanogel with low levels of emulsifiers. The oil-in-water nanogel is thickened by an oil phase and a silicone component that self-structure to increase the complex viscosity of the composition and form the nanogel. The pre-emulsion, containing the silicone component, the oil phase and a water phase, is subjected to a high shear and high pressure treatment. The compositions exemplified in this document comprise an anionic surfactant. Furthermore, one drawback of the method is that the high shear/pressure method of gel formation is requiring high energy and is therefore cost ineffective.

Thus, all mentioned prior arts have limited application because they comprise at least one charged surfactant, anionic and/or cationic, susceptible to interact with the consumer product formulation when they are included therein.

There is therefore a need to provide a composition compatible with different applications which would exhibit enhanced performance for example in terms of fragrance performance on different substrates such as fabrics, skin or hairs and would have stable suspending properties to be able to e.g. suspend microcapsules therein.

The ringing gel composition of the invention solves this problem as it enhances the fragrance performance compared to a microemulsion system and demonstrates suspending properties for solid particles while showing a low viscosity at zero shear with an uncharged system.

SUMMARY OF THE INVENTION

A first aspect of the present invention is therefore a ringing gel composition having a viscosity comprised between 0.1 and 1000 Pa·s at 0.01 s$^{-1}$ shear rate at 20° C. and a viscoelastic dynamic behavior, said composition comprising:
  an aqueous phase,
  a surfactant system essentially consisting of one or more than one non-ionic surfactant, wherein the surfactant system has a mean HLB between 10 and 14,
  a linker chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof, and
  an oil phase comprising a hydrophobic active ingredient, preferably a perfume oil.

A second aspect of the present invention is a microcapsule dispersing system comprising a ringing gel as defined in the invention.

A third object of the present invention is a consumer product comprising the ringing gel composition or the microcapsule dispersing system as defined above.

Finally, a last object of the present invention is the use of a ringing gel composition having a viscosity comprised between 0.1 and 1000 Pa·s at 0.01 s$^{-1}$ shear rate at 20° C. and a viscoelastic dynamic behavior, said composition comprising:
  an aqueous phase,
  a surfactant system essentially consisting of one or more than one non-ionic surfactant, wherein the surfactant system has a mean HLB between 10 and 14,
  a linker chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof, and
  an oil phase comprising a hydrophobic active ingredient, preferably a perfume oil.
  for suspending microcapsules without sedimentation in a liquid product.

DETAILED DESCRIPTION OF THE INVENTION

Unless stated otherwise, percentages (%) are meant to designate percent by weight of a composition.

The present invention has now determined a way to improve the deposition of fragrance on a wet substrate or a dry substrate. It has been surprisingly found that a self-thickened composition comprising an essentially non-ionic surfactant system could in fact significantly improve the performance of the active ingredient contained therein while being suitable to be used in all kind of consumer products.

The ringing gel according to the invention has also proven to be particularly suitable to suspend encapsulated materials.

Thus, a first aspect of the present invention is a ringing gel composition having a viscosity comprised between 0.1 and 1000 Pa·s at 0.01 s$^{-1}$ shear rate at 20° C. and a viscoelastic dynamic behavior, said composition comprising:
  an aqueous phase,
  a surfactant system essentially consisting of one or more than one non-ionic surfactant, wherein the surfactant system has a mean HLB between 10 and 14,
  a linker chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof, and
  an oil phase comprising a hydrophobic active ingredient, preferably a perfume oil.

According to the invention, a "ringing gel" should be understood as a specific type of gel having a firm jelly-like consistency that vibrates and returns to its original configuration when lightly tapped.

It is generally built-up of bicontinuous network of branched worm-like micelles or melted cubic phases with bicontinuous structure and appears multicolored when the bulk solution is observed with polarized filters.

The ringing gel of the present invention is a physical gel characterized by several rheological parameters, defined notably by its low viscosity (when compared to liquid crystalline phases for example) and its viscoelastic behavior under dynamic rheological conditions.

Steady-state and dynamic viscosities were measured by using the rheometer AR-2000 model of TA Instruments V5.4.0. The experiments were realized with a steel cone 40 mm with an angle of 2°. The gap between the cone and the plate, on which the composition is deposited, was 52 µm.

Steady State Viscosity: Non-Newtonian Behavior

According to the invention, the flow behavior of the ringing gel is non-Newtonian, shear thinning with an apparent yield stress. The viscosity values at 20° C. at 0.01 s$^{-1}$ shear rate are comprised between 0.1 and 1000 Pa·s, preferably between 1 and 100 and more preferably between 10 and 100 Pa·s.

Figure 1:
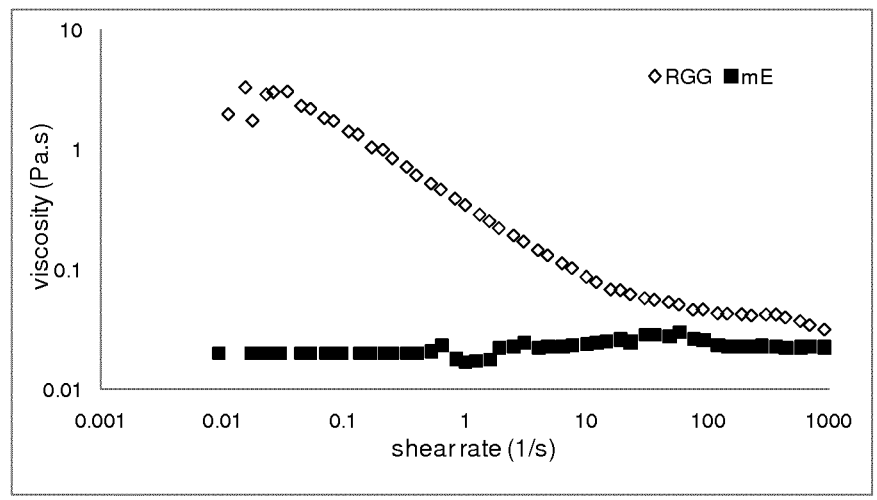
FIG. 1a is a plot of viscosity versus shear rate for a ringing gel (RGG) according to the present invention and for a microemulsion (mE).
FIG. 1b is a plot of the viscosity as function of the stress for a ringing gel (RGG) according to the present invention. The value of the stress corresponding to the maximum of the viscosity is the yield stress.
Figure 1:
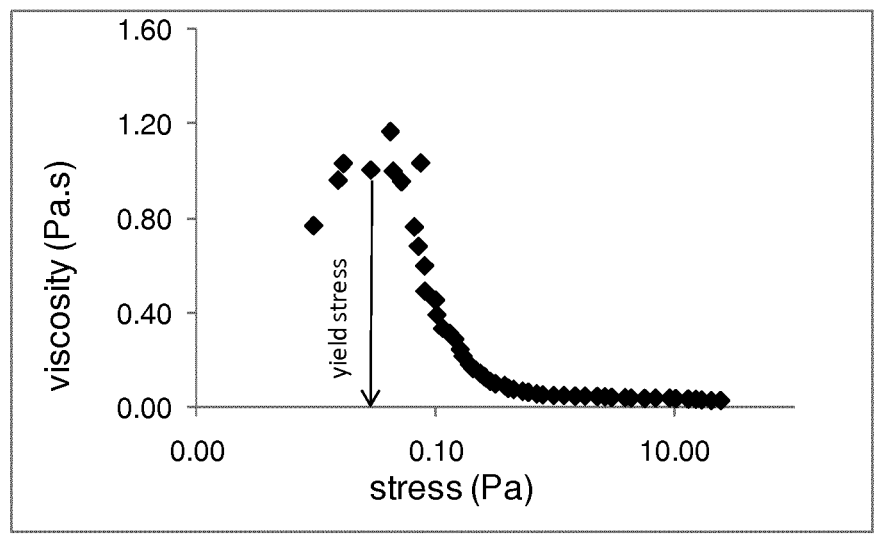

A typical curve of the viscosity as function of the shear rate is represented on FIG. 1a.

The ringing gel according to the invention can also be defined as having a Bingham plastic flow behavior that is well-known by the person skilled in the art.

It means that the ringing gel according to the invention does not flow unless subjected to sufficient shear stress.

A typical curve of the viscosity as function of the stress is represented on FIG. 1b.

Dynamical Viscosity: Storage Modulus G', Loss Modulus G'', Quality Factor Q, and Relaxation Times τ

Storage Modulus G', Loss Modulus G''

The ringing gel has a viscoelastic behavior, studied by applying sinusoidal deformations (strain) at different angular frequencies ω. The shear stress developed by the system in response to the deformations is also a sinusoidal, which is out of phase with the strain. The complex shear modulus is G*=G'+iG'', where G' and G'' are defined as a storage and a loss modulus, respectively. The elasticity (G') and the viscosity (G") of the material are expressed by these two moduli.

Figure 2:
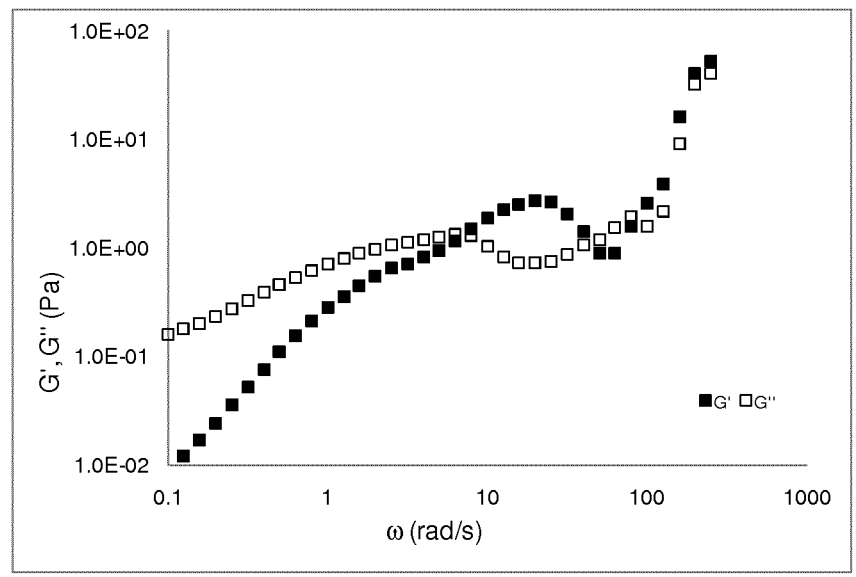
FIG. 2 is a plot of modulii versus angular frequency for a ringing gel (RGG) according to the present invention.

The typical viscoelastic behavior of a ringing gel as defined in the present invention under oscillatory deformations at different frequencies is presented on FIG. 2. The frequency sweep was performed at a fixed stress equal to 1 Pa and at angular frequencies in the range from 0.1 to 500 rad/s. The temperature is kept constant at 20° C. At low oscillation frequencies, the gel behaves as a viscous fluid with G">G'. Then, at a given angular frequency, the elastic modulus G' overcomes the viscous modulus G" and reaches a plateau or a maximum. Further, at high oscillation frequencies, a next crossing between G' and G" appears.

Relaxation Times $\tau$

The crossing points of the curves $G',G"=f(\omega)$ determine the relaxation times of the material as the value reciprocal to the angular frequency.

The first crossing point between G' and G" corresponds to the longest relaxation time ($\tau_1$) of the internal structure indicating the so called "transition to flow". The second cross point corresponds to the shortest relaxation time and indicates the so-called "leathery transition" of the material.

The ringing gel is characterized by a low relaxation time ($\tau_1$) (typically $\tau_1$=0.05–0.5 s).

Quality Factor Q

«Ringing» is a term used in the present invention to mention the ability of the gel to vibrate in a specific range of frequencies and thus to keep the internal structure intact. The quality factor, which is defined in the literature as Q=G'/G" determines the ability of the system to propagate mechanical waves.

The gel of the invention is characterized with a quality factor, which increases as function of the angular frequency and reaches a maximum above 0.5, preferably above 1 (typically in frequency between 5-500 rad/s (1-80 Hz), preferably between 5-300 rad/s and even more preferably between 5-150 rad/s) where the gel is highly elastic leading to the observed vibrations.

Then, after the second crossing point where both G' and G" increase strongly, a decrease of Q is observed.

Thus, when we consider a ternary phase diagram (Water/surfactant/oil phase), the ringing gel of the present invention is a structured liquid between a discontinuous microemulsion or nanoemulsion and a liquid-crystalline phase (lamellar, hexagonal and cubic).

In other words, the ringing gel of the invention is neither an emulsion nor liquid crystalline phases.

Indeed, the discontinuous microemulsions are Newtonian fluids with viscosity independent on the shear rate of the deformation applied. The value of the zero shear viscosity is very low (typically 0.001-1 Pa·s) and the elastic modulus G' is negative.

Furthermore, contrary to the ringing gel, a microemulsion does not have a viscoelastic behavior.

Regarding the liquid crystalline phases (lamellar, hexagonal, cubic), they are highly viscous (typically with a viscosity at 0.01 s$^{-1}$ shear rate (20° C.) greater than 1000 Pa·s).

According to the invention, the mixture (surfactant+linker) must have a suitable Packing parameter in order to form a suitable branched structure as defined above.

Typically, the packing parameter satisfies the following equation:

⅓<P(linker+surfactant)<½.

The "packing parameter" (P) is defined in the literature by the following equation: P=V/LA where V is the volume of the hydrophobic tail of the molecule, l is the effective length of the hydrophobic tail, and A is the area occupied by the hydrophilic head group. These dimensions can be calculated from physical measurements as described in the literature and have been published for different compounds.

According to an embodiment, the system consisting of the surfactant system and the linker has an HLB (S+L) comprised between 11.5 and 13.5, wherein HLB(S+L)=X(surfactant system)*HLB(surfactant system)+Y(linker)*HLB(linker)

with
X(surfactant system) and Y(linker) are the weight concentrations of the surfactant system and linker respectively in the mixture of surfactant system and linker, and X(surfactant system)+Y(linker)=1.

According to another embodiment, the weight ratio surfactant system/(oil phase+linker) is comprised between 0.5 and 4, preferably between 0.8 and 2.

The ringing gel composition according to the invention can comprise a solvent, preferably in an amount up to 40% by weight based on the total weight of the composition.

According to an embodiment, the solvent is present in an amount up to 30% by weight based on the total weight of the composition.

According to another embodiment, the solvent is present in an amount between 10 and 25% by weight based on the total weight of the composition.

Suitable solvents used in the present invention include for example propylene glycol, glycerol, and a mixture thereof.

According to an embodiment, the ringing gel composition comprises:
- 45-99%, preferably 48-97%, more preferably 60-90% by weight of the aqueous phase,
- 3-50%, preferably 4-30%, by weight of the surfactant system as defined above,
- 0.1-35%, preferably 0.15-20% by weight of the linker as defined above
- 0.01-30%, preferably 0.1-20% by weight of the oil phase, and
- 0-40%, preferably 0-30%, more preferably 10-25% by weight of the solvent, based on the total weight of the composition.

According to a particular embodiment, the ringing gel is free from a thickener. A thickener can be defined as any substance suitable to increase the viscosity of a fluid (for example acrylate polymer, structuring gums (xanthan gum), starch, agar, hydroxyl allyl cellulose).

According to an embodiment, the ringing gel composition is free from a silicone component.

The surfactant system according to the invention essentially consists of one or more than one non-ionic surfactants having a mean HLB between 10 and 14.

One or a combination of non-ionic surfactants having a HLB between 10 and 14 can be used.

Thus, if the surfactant system comprises one non-ionic surfactant, mean HLB corresponds to the HLB of the non-ionic surfactant.

On the other hand, if the surfactant system comprises more than one non-ionic surfactant (n non-ionic surfactants), mean HLB is the mean of the HLB values of the surfactants.

$$HLBmean = \sum_{i}^{n} X_i HLB_i$$

where $X_i$ are the weight concentrations of the surfactants in the surfactant system.

As non-limiting examples of non-ionic surfactants, one may cite those belonging to the classes of:

ethoxylated aliphatic $C_6$-$C_{20}$ alcohols containing 2 to 30 EO and/or PO units (EO being ethyleneoxide and PO being propylene oxide) and in particular a $C_{11-15}$ alcohol ether with 9 EO units (such as Tomadol® 1-9 or Tomadol® 25-9), $C_{11-15}$ alcohol ether with 8 EO units (Neodol 91-8), a butyl alcohol ether with 24 to 27 EO and/or PO oxide units (such as PPG-24 Buteth-26 from Dow Chemical), ethoxylated glycerides and mixtures thereof, POE/PPG ethers, $C_8$-$C_{20}$ mono and polyglyceryl esters, sucrose ester compounds such as sucrose esters with $C_8$-$C_{20}$ fatty acid (such as sucrose esters with oleic, palmitic or stearic acid, such as a sucrose monopalmitate, e.g. Habo Monoester P90® commercialized by Compass Foods Corporation), polyoxyethylene $C_{16-60}$ hydroxylesters containing 10 to 40 EO units, such as polyoxyethylenesorbitan monooleate (for examples sorbitol monoesters with oleic, myristic, stearic or palmitic acid, e.g. sorbitol monoester with a fatty acid which are polyethoxylated and containing 10 to 40 EO units also known as those known under the tradenames Tweens® by ACROS Organics (Geel, Belgium)), sorbitan ester known under the tradenames Span®, or such as polyethoxylated castor oils triglyceride containing 10 to 40 EO units such as e.g. Cremophor® RH 40 by BASF, $C_{8-22}$-alkyl polyglucosides (such as those sold under the name Plantacare® by BASF); e.g. fatty alcohol glucosides such as $C_8$-$C_{16}$ alkyl glucoside, e.g. decylglucoside (known also as Plantacare® 2000UP), $C_{12}$-$C_{16}$ alkyl glucoside, e.g. laurylglucoside (known also as Plantacare® 1200UP), $C_8$-$C_{16}$ alkyl glucoside, e.g. cocoglucoside (known also as Plantacare® 818UP), $C_8$-$C_{10}$ alkyl glucoside, e.g. caprylyl/caprylglucoside (known also as Plantacare® 810UP); or combination thereof with a fatty acid e.g. cocoglucoside and glyceryl oleate (known also as Lamesoft® PO 65 by BASF), Amine oxides.

According to the invention, the linker is chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof.

One may cite for example sodium salycilate, sodium benzoate, sodium lactate or potassium sorbate as salts of carboxylic acid.

Fatty acids that can be used in the present invention include but are not limited to lauric acid, myristic acid, palmitic acid esters, and mixtures thereof.

According to an embodiment, the linker is an alcohol with a long alkyl chain.

By "alcohols with long alkyl chains", it means that the number of carbon of the alcohol is greater than 9. As an example, one may cite dodecanol, tetradecanol, hexadecanol, docosanol and mixtures thereof.

Preferably, the esters of carboxylic acids are long esters of carboxylic acids (number of carbon greater than 6).

According to an embodiment, the final composition of the ringing gel has a composition in the range: $(0.33-P_L)/(P_S-P_L)<a<(0.5-P_L)/(P_S-P_L)$, where a is the mol fraction of the non-ionic surfactant, $P_S$ is the packing parameter of the non-ionic surfactant and $P_L$ is the packing parameter of linker. The mol fractions of the linker are equal to $(1-a)$.

According to the intended use of application, the ringing gel composition can comprise additional components.

One may cite, as non-limiting examples of additional components, mineral and/or vegetal oils, pigments, inorganic particles, electrolytes, bleaching agents, emollients, cooling agents and mixtures thereof.

Hydrophobic active ingredients are preferably chosen from the group consisting of flavor, flavor ingredients, perfume, perfume ingredients, essential oils, nutraceuticals, cosmetics, insect control agents, biocide actives and mixtures thereof.

The nature and type of the insect control agents present in the hydrophobic internal phase do not warrant a more detailed description here, which in any case would not be exhaustive, the skilled person being able to select them on the basis of its general knowledge and according to intended use or application.

Examples of such insect control agents are birch, DEET (N,N-diethyl-m-toluamide), essential oil of the lemon *eucalyptus* (*Corymbia citriodora*) and its active compound p-menthane-3,8-diol(PMD), icaridin (hydroxyethyl isobutyl piperidine carboxylate), Nepelactone, Citronella oil, Neem oil, Bog Myrtle (*Myrica Gale*), Dimethyl carbate, Tricyclodecenyl allyl ether, IR3535 (3-[N-Butyl-N-acetyl]-aminopropionic acid, ethyl ester, Ethylhexanediol, Dimethyl phthalate, Metofluthrin, Indalone, SS220, anthranilate-based insect repellents, and mixtures thereof.

According to a particular embodiment, the hydrophobic-active ingredient comprises a mixture of a perfume with another ingredient selected from the group consisting of nutraceuticals, cosmetics, insect control agents and biocide actives.

According to a particular embodiment, the hydrophobic active ingredient comprises a perfume.

According to a particular embodiment, the hydrophobic active ingredient consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or *sulphurous* heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate.

As mentioned previously, it has been found that a ringing gel composition comprising a non-ionic surfactant system consisting essentially of non-ionic surfactant(s) could improve the performance of the active ingredient contained therein.

Furthermore, it has surprisingly been found that the ringing gel of the present invention has advantageous properties such as suspending properties for solid particles in particular for microcapsules without showing signs of instability, even in the absence of a thickener.

Indeed, due to the internal branched structure, the ringing gel is able to retain microcapsules in stable suspension without the need of a thickener. On the contrary, any system free of charge such as microemulsion requires the use of thickener to retain particles.

Thus, according to an embodiment, the ringing gel composition comprises one part of the oil phase freely dispersed in the water phase and another part of the oil phase dispersed in an encapsulated form in the water phase.

According to a particular embodiment, the ringing gel comprises a perfume freely dispersed and an encapsulated perfume in the form of microcapsules.

The encapsulated form can be microcapsules which have been widely described in the prior art. One may cite for example the core-shell type with a polymeric shell or microcapsules having a polymer matrix The nature of the polymeric shell from the microcapsules of the invention can vary. As non-limiting examples, the shell can be aminoplast-based, polyurea-based or polyurethane-based. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to an embodiment, the shell comprises an aminoplast copolymer, such as melamine-formaldehyde or urea-formaldehyde or cross-linked melamine formaldehyde or melamine glyoxal.

According to another embodiment the shell is polyurea-based made from, for example but not limited to isocyanate-based monomers and amine-containing crosslinkers such as guanidine carbonate and/or guanazole. Preferred polyurea microcapsules comprise a polyurea wall which is the reaction product of the polymerisation between at least one polyisocyanate comprising at least two isocyanate functional groups and at least one reactant selected from the group consisting of an amine (for example a water soluble guanidine salt and guanidine); a colloidal stabilizer or emulsifier; and an encapsulated perfume. However, the use of an amine can be omitted.

According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). According to another embodiment, the emulsifier is an anionic or amphiphilic biopolymer preferably chosen from the group consisting of gum Arabic, soy protein, gelatin, sodium caseinate and mixtures thereof.

According to another embodiment, the shell is polyurethane-based made from, for example but not limited to polyisocyanate and polyols, polyamide, polyester, etc.

The preparation of an aqueous dispersion/slurry of core-shell microcapsules is well known by a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together
- a) a polyamine component in the form of melamine or of a mixture of melamine and at least one $C_1$-$C_4$ compound comprising two $NH_2$ functional groups;
- b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
- c) a protic acid catalyst;

2) preparing an oil-in-water dispersion, wherein the droplet size is comprised between 1 and 600 um, and comprising:
- i. an oil;
- ii. a water medium
- iii. at least an oligomeric composition as obtained in step 1;
- iv. at least a cross-linker selected amongst
  - A) $C_4$-$C_{12}$ aromatic or aliphatic di- or tri-isocyanates and their biurets, triurets, trimmers, trimethylol propane-adduct and mixtures thereof; and/or
  - B) a di- or tri-oxiran compounds of formula

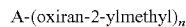

wherein n stands for 2 or 3 and 1 represents a $C_2$-$C_6$ group optionally comprising from 2 to 6 nitrogen and/or oxygen atoms;
- v. optionally a $C_1$-$C_4$ compounds comprising two $NH_2$ functional groups;

3) Heating said dispersion;
4) Cooling said dispersion.

This process is described in more details in WO 2013/068255, the content of which is included by reference.

According to another embodiment, the shell of the microcapsule is polyurea- or polyurethane-based. Examples of processes for the preparation of polyurea and polyureathane-based microcapsule slurry are for instance described in WO2007/004166, EP 2300146, EP2579976 the contents of which is also included by reference. Typically a process for the preparation of polyurea or polyurethane-based microcapsule slurry include the following steps:

a) Dissolving at least one polyisocyanate having at least two isocyanate groups in an oil to form an oil phase;
b) Preparing an aqueous solution of an emulsifier or colloidal stabilizer to form a water phase;
c) Adding the oil phase to the water phase to form an oil-in-water dispersion, wherein the mean droplet size is comprised between 1 and 500 µm, preferably between 5 and 50 µm;
d) Applying conditions sufficient to induce interfacial polymerisation and form microcapsules in form of a slurry.

Being free of charge, the ringing gel of the present invention can be used in many fields of application.

For example, many consumers demand more and more an intense and strong perfume scent to their laundry.

Thus, another object of the present invention is a ringing gel composition as defined above in the form of a laundry scent booster.

Another object of the invention is a microcapsule dispersing system comprising a ringing gel according to the invention and at least one microcapsule as defined previously.

Another object of the present invention is a process for preparing a ringing gel composition according to the present invention, said process comprising the step of mixing an aqueous phase, a surfactant system, a linker, an oil phase comprising a hydrophobic active ingredient, and optionally a solvent, wherein:

the surfactant system essentially consisting of one or more than one non-ionic surfactant, wherein the surfactant system has a mean HLB between 10 and 14, the linker is chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof.

According to a particular embodiment, the linker is separately dissolved in the oil phase comprising the hydrophobic active ingredient due to its higher solubility in the oil phase.

According to the invention, the process does not require any shear and/or pressure treatment to induce the formation of the gel.

The invention's ringing gel composition can advantageously be used in many application fields and used in various consumer products.

Thus, another object of the invention is a consumer product comprising or consisting of the ringing gel composition as defined above or prepared according to the process defined above.

According to an embodiment, the consumer product is in the form of a home care or personal care product selected from the group consisting of a skin cleansing product, a shampoo, a rinse-off conditioner, a deodorant, an antiperspirant, a body lotion, a leave-on conditioner, a fabric conditioner, a liquid detergent, a laundry scent booster and an all propose cleaner.

According to a particular embodiment, the consumer product is a laundry scent booster.

As mentioned previously, the ringing gel composition of the present invention has shown its capability to suspend, for instance microcapsules, without sedimentation over a long period of time.

Thus, another object of the invention is a method for suspending microcapsules without sedimentation in a liquid comprising the step consisting of:

providing a ringing gel composition having a viscosity comprised between 0.1 and 1000 Pa·s at 0.01 s$^{-1}$ shear rate at 20° C. and a viscoelastic dynamic behavior, said composition comprising:

an aqueous phase, a surfactant system essentially consisting of one or more than one non-ionic surfactant, wherein the surfactant system has a mean HLB between 10 and 14, a linker chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof, and an oil phase comprising a hydrophobic active ingredient, preferably a perfume oil, and mixing microcapsules in said composition.

Finally, a last object of the present invention is the use of a ringing gel composition having a viscosity comprised between 0.1 and 1000 Pa·s at 0.01 s$^{-1}$ shear rate at 20° C. and a viscoelastic dynamic behavior, said composition comprising:

an aqueous phase, a surfactant system essentially consisting of one or more than one non-ionic surfactant, wherein the surfactant system has a mean HLB between 10 and 14, a linker chosen in the group consisting of alcohols, salts and esters of carboxylic acids, salts and esters of hydroxyl carboxylic acids, fatty acids, fatty acid salts, glycerol fatty acids, surfactant having an HLB less than 10 and mixtures thereof, and an oil phase comprising a hydrophobic active ingredient, preferably a perfume oil for suspending without sedimentation a solid or a liquid.

The invention will now be further described by way of examples. It will be appreciated that the invention as claimed is not intended to be limited in any way by these examples.

Example 1

Preparation of the Ringing Gel Composition According to the Invention

Different fragrances used in the examples are summarized in table 1 below.

TABLE 1

| compositions of fragrances | | | | | |
|---|---|---|---|---|---|
| Fragrance A | | Fragrance B | | Fragrance C | |
| Ingredient | % wt | Ingredient | % wt | Ingredient | % wt |
| Hedione ®[1] | 10 | Benzyl acetate | 20 | Hedione ®[1] | 1 |
| Habanolide ®[2] | 6 | Exaltolide[8] | 10 | Habanolide ®[2] | 20 |
| Helvetolide ®[3] | 4 | Ambrox ®[9] | 2 | Exaltolide[8] | 60 |
| Muscenone delta[4] | 1 | Neobutenone ®[10] | 0.1 | Ambrox ®[9] | 1 |
| Dihydromyrcenol[5] | 2 | Helvetolide ®[3] | 4 | Helvetolide ®[3] | 6 |
| Citronellol BJ | 2 | Dihydromyrcenol[11] | 20 | Muscenone delta[4] | 12 |
| Phenethylol | 20 | Coranol[12] | 10 | | |
| Benzyl acetate | 6 | IsoEsuper[7] | 26 | | |
| Geraniol | 10 | Dipropylene glycol | 7.9 | | |
| Florol ®[6] | 12 | | | | |
| IsoEsuper[7] | 2 | | | | |
| Dipropylene glycol | 25 | | | | |
| Log P (mean) | 1.9 | | 3.7 | | 5.7 |

[1] Methyl dihydrojasmonate (Origin: Firmenich SA, Geneva, Switzerland)
[2] pentadecenolide (Origin: Firmenich SA, Geneva, Switzerland)
[3] (1S,1'R)-2-[1-(3',3'-dimethyl-1'-cyclohexyl)ethoxy]-2-methylpropyl propanoate (Origin: Firmenich SA, Geneva, Switzerland)
[4] 3-Methyl-5-cyclopentadecen-1-one (Origin: Firmenich SA, Geneva, Switzerland)
[5] Origin: International Flavors & Fragrances, USA
[6] tetrahydro-2-isobutyl-4-methyl-4(2H)-pyranol (Origin: Firmenich SA, Geneva, Switzerland)
[7] 1-(octahydro-2,3,8,8-tetramethyl-2-naphtalenyl)-1-ethanone (Origin: International Flavors & Fragrances, USA)
[8] pentadecanolide (Origin: Firmenich SA, Geneva, Switzerland)
[9] (−)-(8R)-8,12-epoxy-13,14,15,16-tetranorlabdane (Origin: Firmenich SA, Geneva, Switzerland)
[10] 1-(5,5-dimethyl-1-cyclohexen-1-yl)-4-penten-1-one (Origin: Firmenich SA, Geneva, Switzerland)
[11] Origin: International Flavors & Fragrances, USA
[12] 4-cyclohexyl-2-methyl-2-butanol (Origin: Firmenich SA, Geneva, Switzerland)

Different ringing gel compositions were prepared (compositions 1-5—see table 2) according to the following protocol.

In a first step, the aqueous phase (water), the solvent (propylene glycol) if present and surfactants were mixed together at room temperature under agitation with magnetic stirrer at 300 rpm for 5 min.

In a second step, the linker was dissolved in the hydrophobic active ingredient (fragrance) at room temperature under agitation with magnetic stirrer at 300 rpm. The resulting mixture was mixed for 5 min.

Then, the aqueous phase and the oil phase were mixed together at room temperature for 5 min leading to the formation of a transparent or opalescent ringing gel.

TABLE 2

| Ringing gel compositions | | | | | | |
|---|---|---|---|---|---|---|
| Composition | | 1 | 2 | 3 | 4 | 5 |
| Aqueous phase | Water | 71.20% | 89.5% | 78.8% | 79.4% | 70% |
| solvent | Propylene glycol | 20.30% | — | — | — | 20% |
| Surfactants | Deceth-8[1] | 4.00% | 6% | | | |
| | Laureth-9[1] | | | | | 4.00% |
| | Plantacare 2000UP[2] | | | 8.30% | 7.7% | |
| Linker | Deceth-3[1] | 1.50% | | | | |
| | Lauryl lactate | | | | 1% | |
| | Lauric acid | | 1.5% | 1.60% | | |
| | Glyceryl Caprylate | | | | | 3.00% |
| Hydrophobic active ingredient | Fragrance B | 3.00% | 3.0% | 3.00% | 3.00% | 3.00% |

TABLE 2-continued

| Ringing gel compositions | | | | | |
|---|---|---|---|---|---|
| Composition | 1 | 2 | 3 | 4 | 5 |
| Viscosity (Pa · s) (at 0.015 s$^{-1}$ shear rate) | 1.72 | 10.54 | 60 | 2.88 | 5.0 |

[1] polyethylene glycol ethers of decyl alcohol (KLK Oleo)
[2] alkyl polyglucoside C8-C10 (BASF)

Example 2

Preparation of Ringing Gel Compositions Using Different Fragrances

Three different ringing gel compositions were prepared according to the protocol described in example 1 with fragrances having different Log P (see table 1).

Compositions of these ringing gels are summarized in table 3 below.

TABLE 3

| Ringing gel compositions | | | |
|---|---|---|---|
| | Fragrance A % wt | Fragrance B % wt | Fragrance C % wt |
| Aqueous phase (Water) | 70.64 | 70.78 | 71.07 |
| solvent (Propylene glycol) | 20.18 | 20.22 | 20.30 |
| Non-ionic surfactant (Deceth-8) | 4.04 | 4.04 | 4.06 |

TABLE 3-continued

Ringing gel compositions

|  | Fragrance A % wt | Fragrance B % wt | Fragrance C % wt |
|---|---|---|---|
| Linker (Deceth-3) | 1.51 | 1.52 | 1.52 |
| Hydrophobic active ingredient (Fragrance) | 3.63 | 3.44 | 3.05 |

The obtained ringing gels were slightly opalescent.

These results underline that ringing gel compositions according to the invention can be prepared with fragrances covering a broad log P range.

Example 3

Performance as Fragrance Booster

Ringing Gel Compositions According to the Invention Versus Microemulsion

Experimental Protocol

The olfactive performance of ringing gel compositions formulated as described in the invention was compared with a microemulsion comprising the same components but in different proportions (see table 4).

TABLE 4

Ringing gel (according to the invention) and microemulsion compositions

|  | Ringing gel (RGG) | Microemulsion (mE) |
|---|---|---|
| Aqueous phase (Water) | 70% | 45% |
| solvent (Propylene glycol) | 20% | 45% |
| Non-ionic surfactant (Deceth-8) | 6% | 6% |
| Hydrophobic active ingredient (Fragrance[4]) | 2.7% | 2.7% |
| Linker (Lauric acid) | 1.3% | 1.3% |

[4]Fragrance A or Fragrance B or Fragrance C

The microemulsion is a transparent solution, containing discontinuously dispersed nanometric droplets of oil compound. In contrast, the ringing gel is an opalescent solution, composed of a network of branched micelles.

The olfactive performance was evaluated on wet clothes and after 1 day of drying. Cotton terry towels (10 pieces, 18 cm*18 cm, about 30 g each) were washed with 30 g of unperfumed detergent in a washing machine (Miele Novotronic W300-33CH) at 40° C. using the short cycle program. The wash was followed by a rinse at 900 rpm with 10 g of the ringing gel or the microemulsion (see table 4).

The terry towels were evaluated wet or they were then line dried for 24 hours before being evaluated.

Results

The intensity of the perception of the perfume on the wet or dry towels treated with the ringing gel or the microemulsion was evaluated by a panel of 20 trained panelists. They were asked to rate the intensity of the perfume perception on a scale ranging from 0 to 10, wherein 0 means no odour and 10 means very strong odour. The results are summarized in the Table 5.

TABLE 5

Perfume intensity from ringing gel (RGG) and microemulsion (mE) (wet and dry conditions)

|  | Wet | | Dry | |
|---|---|---|---|---|
|  | RGG | mE | RGG | mE |
| Fragrance A | 5.6 | 5.3 | 2.1 | 1.9 |
| Fragrance B | 5.2 | 4.7 | 5.8 | 5.3 |
| Fragrance C | 4.9 | 4.6 | 4.2 | 4.3 |

Conclusions

The use of the ringing gel according to the invention exhibits a better perfume intensity (both for dry and wet conditions) when compared to a microemulsion underlying a better long-lasting performance for the ringing gel.

Example 4

Viscoelastic Behavior of the Ringing Gel According to the Invention

Two types of rheology studies were performed to characterize the ringing gel of the present invention: steady state studies and oscillatory shear studies.

Steady-state and dynamical viscosities were measured by using the rheometer AR-2000 model of TA Instruments V5.4.0. The experiments were realized with a steel cone 40 mm with an angle of 2°. The gap between the cone and the plate, on which the composition is deposited, was 52 μm.

In steady state rheological measurements, the effect of viscosity and shear stress as a function of shear rate was measured. The shear rate was varied from 0.001 (1/s) to 1000 (1/s) and the temperature was held constant at 20° C.

In oscillatory shear measurement studies, a small angle sinusoidal deformation was applied to the sample so as not to disturb fluid structure. The rheometer was operated in dynamic mode and the viscoelastic modulii (G' and G") were measured as a function of oscillation frequency. The range of oscillation frequency was varied from 0.1 rad/s to 500 rad/s.

FIG. 1a shows the steady shear rate viscosity curve for the ringing gel and the microemulsion having the compositions detailed in table 4. These curves underline that the ringing gel of the invention has a non-Newtonian behavior whereas the microemulsion exhibits a Newtonian behavior.

FIG. 1b shows the viscosity as a function of the shear stress. The peak of the viscosity corresponds to the value of the yield stress indicating a Bingham-type of fluid.

FIG. 2 shows the dynamic shear modulii for the ringing gel having the compositions detailed in table 4. It shows again the typical viscoelastic behavior of the ringing gel of the invention, having two relaxation times ($\tau_1$=0.16 s and $\tau_2$=0.025 s) and strong increase of both G' and G" at high frequencies in the acoustic range (>100 rad/s).

Figure 3:
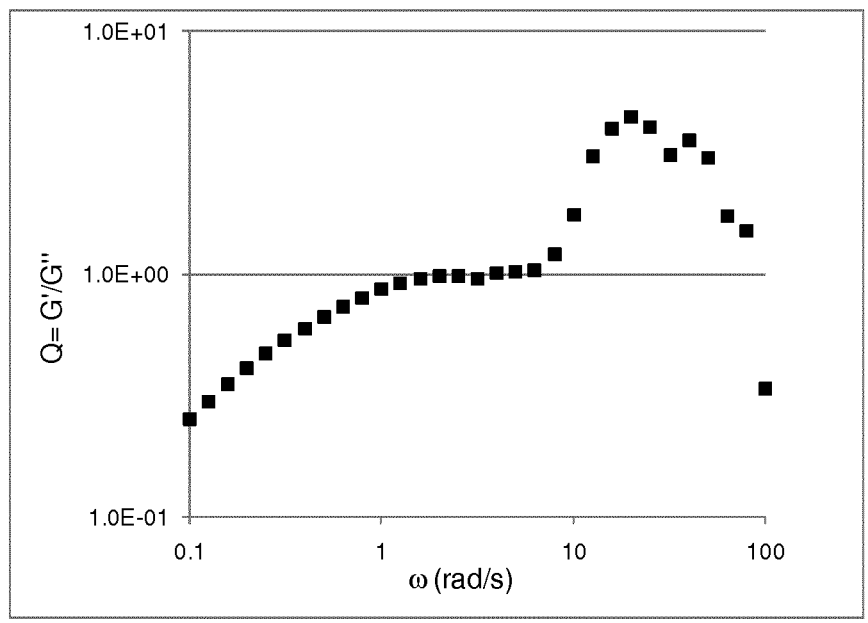
FIG. 3 is a plot of quality factor (Q) versus angular frequency for a ringing gel (RGG).

FIG. 3 shows the quality factor, which is defined in the literature as Q=G'/G" versus the angular frequency.

The gel of the invention is characterized by a quality factor which increases as function of the angular frequency and reaches a maximum greater than 1 in the range of 20 rad/s. After the second crossing point where G' and G" increase strongly, Q decreases.

All of these rheological parameters underline that the ringing gel of the invention has a viscoelastic behavior contrary to a microemulsion.

Example 5

A Ringing Gel Comprising Microcapsules Versus a Microemulsion Comprising Microcapsules Preparation of Microcapsule Slurry a Microcapsules having the following composition (see table 6) were prepared according to the process described below.

TABLE 6

Composition of capsule slurry A

| Ingredient | Capsule A Amount [%] |
|---|---|
| Oil Phase | 30.9 |
| Perfume oil[1] | 30.28 |
| Polyisocyanate[2] | 0.62 |
| Water phase | |
| Acrylamide and acrylic acid copolymer[3] | 4.7 |
| Melamine-formaldehyde resins[4] | 4.7 |
| Water | 59 |
| Sodium hydroxide | 0.5 |
| Acetic acid | 0.2 |
| Total | 100 |

[1] see Table 7
[2] Takenate ® D-110N; origin: Mitsui Chemicals
[3] Alcapsol from Ciba, 20% solution in water
[4] 90/10 blend of Cymel 385 & Cymel 9370 from Cytec, both 70% solution in water

TABLE 7

Perfume oil composition

| Ingredients | Wt % |
|---|---|
| Ethyl 2-methylbutyrate | 5.2% |
| Amyl acetate | 2.5% |
| Aldehyde C 8 | 3.1% |
| Hexyl acetate | 9.7% |
| Methylparacresol | 1.0% |
| Limonene | 3.7% |
| Amyl butyrate | 1.0% |
| Aldehyde C 9 | 2.85% |
| 2,4-Dimethyl-3-cyclohexene-1-carbaldehyde[1] | 2.75% |
| Eucalyptol | 8.5% |
| Menthone | 0.4% |
| Allyl heptanoate | 8.0% |
| Aldehyde C 10 | 9.0% |
| Aldehyde MNA[2] | 3.2% |
| Delta damascone | 5.9% |
| Yara Yara | 5.4% |
| Neobutenone ®[3] | 1.0% |
| Isoraldeine70 | 5.0% |
| Lilial ®[4] | 8.5% |
| Undecalactone gamma | 8.5% |
| Norlimbanol ®[5] | 0.9% |
| Benzyl benzoate | 3.9% |
| Total | 100.0% |

[1] Firmenich SA, Geneva, Switzerland
[2] 2-méthylundécanal
[3] 1-(5,5-dimethyl-1-cyclohexen-1-yl)-4-penten-1-one, Firmenich SA, Geneva, Switzerland
[4] 3-(4-tert-butylphenyl)-2-methylpropanal, Givaudan SA, Vernier, Switzerland
[5] trans-1-(2,2,6-trimethyl-1-cyclohexyl)-3-hexanol, Firmenich SA, Geneva, Switzerland The oil phase was prepared by admixing a polyisocyanate (trimethylol propane adduct of xylylene diisocyanate, Takenate® D-110N, origin: Mitsui Chemicals) with a perfume oil comprising the ingredients listed in Table 7. The oil phase consists of 2% Takenate® D-110N and 98% of the perfume oil. Preferably, at least one polyisocyanate like Takenate D-110N is added in an amount comprised between 0.1% and 10%, preferably between 0.5% and 5%. After encapsulation and use of the Takenate D-110N to cross-link the melamine/formaldehyde wall, the residual level of unreacted polyisocyanate in the perfume oil is very low and therefore the internal core of the capsule is only made of the perfume oil.

To make the capsule slurry, the acrylamide and acrylic acid copolymer and the melamine-formaldehyde resin were dissolved in water to form the water phase. Then the perfume premix oil was added into this solution and the pH was regulated to 5 with acetic acid. The temperature was raised to 90° C. for 2 hours to allow the curing of the capsules. At this point, capsules are formed, cross-linked and stable. Then a solution of ethylene urea (containing about 3% w/w of ethylene urea relative to the weight of the slurry) was added as usually done with aminoplast capsules as an agent to scavenge residual free formaldehyde and the mixture was left to cool down to room temperature. The final pH was adjusted to 7 with sodium hydroxide.

2% by weight of microcapsule slurry A were added into the composition of the ringing gel as detailed in table 4.

In a second experiment, 2% of microcapsule slurry A were added into the composition of the microemulsion as detailed in table 4.

Figure 4:
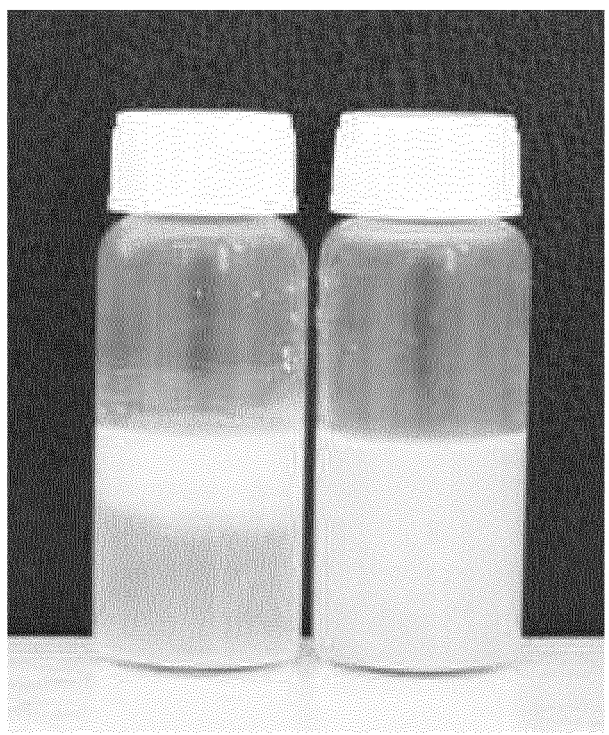
FIGS. 4a and 4b are pictures representing respectively a microemulsion (left) comprising 2% of microcapsules and a ringing gel (right) according to the invention comprising 2% of microcapsules.

FIGS. 4a (left) and 4b (right) show respectively the microemulsion and the ringing gel comprising the microcapusles after 1 month of storage at 25° C.

These figures underline that the ringing gel according to the invention is able to suspend microcapsules in a stable manner without sedimentation or flocculation whereas the microcapsules contained in the microemulsion remain at the interface between the air and the microemulsion.

Therefore, the ringing gel of the present invention is entirely suitable for suspending microcapsules without thickener and without sedimentation over a long period of time.

Example 6

Fragrance Release Performance

The fragrance release performance of the ringing gel defined in the present invention was determined and compared with fragrance release when the fragrance is solubilized in a microemulsion comprising a thickener (see table 8).

TABLE 8

Sample composition

| | Function | Ringing Gel Sample A % | Microemulsion Sample B % |
|---|---|---|---|
| Water | Water phase | 61.90 | 63.68 |
| Propylene glycol | Solvent | 21.10 | 21.69 |
| Alcohol 6-12 Ethoxylate[1] | Nonionic surfactant | 9.50 | 9.50 |
| Dodecanoic acid[2] | Linker | 2.50 | 0 |
| Xanthan[3] | Thickener | 0.00 | 0.13 |

TABLE 8-continued

| | | Ringing Gel Sample A | Microemulsion Sample B |
|---|---|---|---|
| | Function | % | % |
| Fragrance[4] | Hydrophobic active ingredient | 5.00 | 5.00 |

[1] Firmenich SA
[2] Firmenich SA
[3] Firmenich SA
[4] Fragrance B (see table 1)

The following different evaluations were made.

1/Fragrance Release Performance of the Ringing Gel Compared to the Microemulsion (not Applied on any Substrate)

The gas concentration of the fragrance above sample A (ringing gel solution) (Cg) is compared to the gas concentration of the same fragrance above the comparative sample B (Cgref). If the value Cg/Cgref is lower than one, it means that there is less fragrance molecules in the headspace above sample A than above comparative sample B. In this case, we can conclude that the analysed ringing gel leads to a better retention. On the contrary, if the value is more than one, fragrance molecules preferably move to the air.

Figure 5:
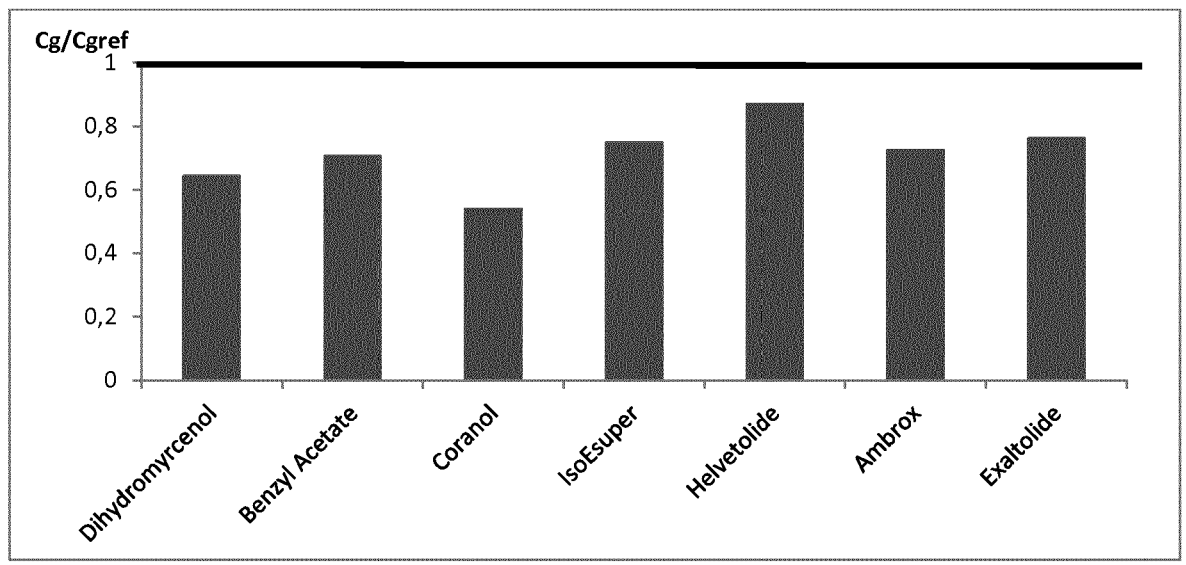
FIG. 5 represents headspace analysis of different raw materials for a ringing gel according to the invention compared to a microemulsion (not applied on any substrate).

As it can be seen from FIG. 5, all values Cg/Cgref for different raw materials are lower than 1 underlying that the ringing gel of the present invention shows a better fragrance retention than the comparative sample B.

2/Fragrance Release Performance of the Ringing Gel Compared to the Microemulsion (Applied on Cotton Towels)

Deposition on fabrics was evaluated directly by analysing the fragrance performance from dried cotton towels. In this experiment, cotton towels (18 cm*18 cm, about 30 g each) were washed in 300× diluted ringing gel or microemulsion, respectively. Then, the towels were let to dry at room temperature during 1 day. Piece of them with a surface 1 cm² was cut and analysed by GC-MS-Headspace analysis.

If the perfume molecules were strongly deposited on the towel, high gas concentration of these molecules is perceived in the headspace. In that case, if the ratio Cg/Cg(ref) is higher than 1, one can conclude that the fragrance performance from the towels washed with the ringing gel is higher compared to comparative sample B. The comparison is made with fragrance performance from dried towels washed with 300× diluted benchmark solution.

Figure 6:
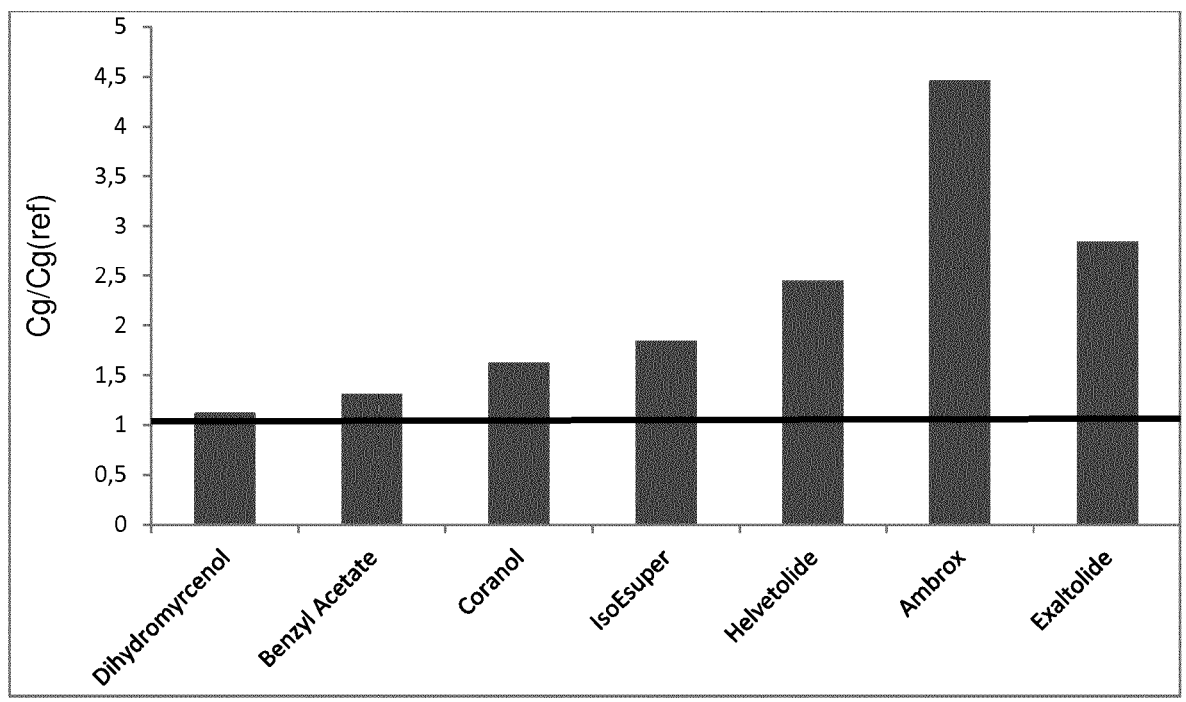
FIG. 6 represents headspace analysis of different raw materials for a ringing gel according to the invention compared to a microemulsion (applied on towels).

As it can be seen from FIG. 6, all values Cg/Cgref for different raw materials are greater than 1 underlying that the ringing gel of the present invention shows a better fragrance deposition than the microemulsion.

3) Fragrance Release Performance of the Ringing Gel Compared to the Microemulsion Assessed in Sensory Test The olfactive performance was evaluated on clothes after 3 days of drying. Cotton terry towels (10 pieces, 18 cm*18 cm, about 30 g each) were washed in a washing machine (Miele Novotronic W300-33CH) at 40° C. using the short cycle program. The wash was followed by a rinse at 900 rpm with 40 g of the ringing gel sample A or the microemulsion sample B (see table 8).

The terry towels were line dried for 3 days and evaluated.

Results

The intensity of the perception of the perfume on dry towels treated with the ringing gel or the microemulsion was evaluated by a panel of 20 trained panelists. They were asked to rate the intensity of the perfume perception on a scale ranging from 0 to 7, wherein 0 means no odour and 7 means very strong odour.

On average the towels rinsed with the ringing gel after 3 days of drying were rated 5.3 while the towels rinsed with the microemulsion were rated 4.5.

Conclusions

The use of the ringing gel according to the invention exhibits a better perfume intensity on dry clothes after 3 days when compared to a microemulsion underlying a better long-lasting performance for the ringing gel.

What is claimed is:

1. A ringing gel composition having a viscosity comprised between 0.1 and 1000 Pa·s at 0.01 s⁻¹ shear rate at 20° C. and a viscoelastic dynamic behavior, said composition comprising:
    an aqueous phase,
    a non-ionic surfactant system consisting of one or more non-ionic surfactants, wherein the surfactant system has a mean HLB between 10 and 14,
    a linker selected from the group consisting of alcohols, fatty acids, glycerol fatty acids, surfactants having an HLB less than 10, and mixtures thereof, and
    an oil phase comprising a hydrophobic active ingredient; wherein the ringing gel composition is free of charge.

2. The ringing gel composition according to claim 1, wherein the non-ionic surfactant system and the linker has an HLB (S+L) between 11.5 and 13.5, wherein:
    HLB(S+L)=X(surfactant system)*HLB(surfactant system)+Y(linker)*HLB(linker) with X(surfactant system) and Y(linker) representing the weight concentrations of surfactant system and linker respectively in the mixture of surfactant system and linker, and
    X(surfactant system)+Y(linker)=1.

3. The ringing gel composition according to claim 1 wherein the weight ratio of the non-ionic surfactant system/ (oil phase+linker) is between 0.5 and 4.

4. The ringing gel composition according to claim 1, further comprising a solvent.

5. The ringing gel composition according to claim 4, wherein the solvent is present in an amount of up to 40% by weight based on the total weight of the composition.

6. The ringing gel composition according to claim 1, comprising:
    45-99% by weight of the aqueous phase,
    3-50% by weight of the non-ionic surfactant system,
    0.1-35% by weight of the linker,
    0.01-30% by weight of the oil phase, and
    0-40% by weight of the solvent, based on the total weight of the composition.

7. The ringing gel composition according to claim 1, wherein the gel has a quality factor Q, defined as a ratio between the elastic G' and viscous G" modulus, greater than 0.5 in the angular frequency range of 5 to 500 rad/s.

8. The ringing gel composition according to claim 1, wherein the non-ionic surfactant is one or more ethoxylated aliphatic alcohols, POE/PPG (polyoxyethylene and polyoxypropylene) ethers, mono and polyglyceryl esters, sucrose ester compounds, polyoxyethylene hydroxylesters, alkyl polyglucosides, amine oxides or combinations thereof.

9. The ringing gel composition according to claim 1, wherein the composition is free from a thickener.

10. The ringing gel composition according to claim 1, wherein one part of the oil phase is freely dispersed in the aqueous phase and another part of the oil phase is dispersed in an encapsulated form in the aqueous phase.

11. A microcapsule dispersing system comprising a ringing gel as defined in claim 10.

12. A consumer product comprising the microcapsule dispersing system according to claim 11.

13. The consumer product according to claim 12, in the form of a home care or personal care product selected from the group consisting of a skin cleansing product, a shampoo, a rinse-off conditioner, a deodorant, an antiperspirant, a body lotion, a leave-on conditioner, a fabric conditioner, a liquid detergent, a laundry scent booster, and an all purpose cleaner.

14. The consumer product according to claim 13, in the form of a laundry scent booster.

15. The ringing gel composition according to claim 1, in the form of a laundry scent booster wherein the hydrophobic active ingredient comprises a perfume.

16. The ringing gel composition according to claim 1, wherein the hydrophobic active ingredient is a perfume oil.

17. A consumer product comprising the ringing gel composition according to claim 1.

18. The consumer product according to claim 17, in the form of a home care or personal care product selected from the group consisting of a skin cleansing product, a shampoo, a rinse-off conditioner, a deodorant, an antiperspirant, a body lotion, a leave-on conditioner, a fabric conditioner, a liquid detergent, a laundry scent booster, and an all purpose cleaner.

19. The consumer product according to claim 18, in the form of a laundry scent booster.

20. A method for suspending microcapsules in a liquid comprising the steps consisting of:
providing a ringing gel composition having a viscosity comprised between 0.1 and 1000 Pa·s at 0.01 s$^{-1}$ shear rate at 20° C. and a viscoelastic dynamic behavior, said composition comprising:
an aqueous phase,
a non-ionic surfactant system consisting of one or more non-ionic surfactants, wherein the surfactant system has a mean HLB between 10 and 14,
a linker selected from the group consisting of alcohols, fatty acids, glycerol fatty acids, surfactants having an HLB less than 10, and mixtures thereof, and
an oil phase comprising a hydrophobic active ingredient, and
mixing microcapsules into said composition;
wherein the ringing gel composition is free of charge.

* * * * *